(12) United States Patent
Yang (10) Patent No.: US 7,801,692 B2
(45) Date of Patent: Sep. 21, 2010

(54) APPARATUS FOR FASTENER INSPECTION AND SORTING

(75) Inventor: Ming-Liau Yang, Kaohsiung County (TW)

(73) Assignee: Te Hung En Enterprise Co., Ltd., Kaohsiung County (TW)

( * ) Notice: Subject to any disclaimer, the term of this patent is extended or adjusted under 35 U.S.C. 154(b) by 359 days.

(21) Appl. No.: 12/046,758

(22) Filed: Mar. 12, 2008

(65) Prior Publication Data
US 2009/0234606 A1    Sep. 17, 2009

(51) Int. Cl.
*G01N 37/00* (2006.01)
*B04C 5/00* (2006.01)

(52) U.S. Cl. .................................... 702/81; 209/929

(58) Field of Classification Search .................... 702/81, 702/33–36, 38, 57, 59, 65, 83–84, 108, 113–114, 702/122, 127, 150–153, 182–183, 188–189; 209/509, 517, 521–522, 526, 529, 538–540, 209/560–562, 690, 929; 198/339.1, 341.01, 198/341.03, 341.07, 341.08, 347.1, 350, 198/358, 570; 470/44–45, 47
See application file for complete search history.

(56) References Cited

U.S. PATENT DOCUMENTS 7,364,043 B2 *   4/2008   Ong et al. .................... 209/652
2006/0244953 A1 * 11/2006   Wei et al. .................... 356/237.1

OTHER PUBLICATIONS

Ukida, H., Visual Defect Inspection of Rotating Scew Heads, Sep. 17-20, 2007, SICE Annual Conference, pp. 1478-1483.*

* cited by examiner

*Primary Examiner*—Michael P Nghiem
*Assistant Examiner*—Toan M Le
(74) *Attorney, Agent, or Firm*—Rosenberg, Klein & Lee (57) ABSTRACT

The present invention pertains to an apparatus for fastener inspection and sorting mainly including an auxiliary device disposed beside the turntable and attached to an inspecting machine. The device has a support base located adjacent to the turntable and a driving assembly mounted on the base. In this manner, the inspecting machine captures defect signals of each object in different orientations by means of the device driving the machine to automatically revolve round the object or by the magnetic attraction assisting in spinning the object when the machine is immobile, thereby transmitting integral signals to the determining machine for an accurate determinations and hence increasing the quality of the inspection and sorting.

8 Claims, 7 Drawing Sheets

APPARATUS FOR FASTENER INSPECTION AND SORTING

BACKGROUND OF THE INVENTION

1. Field of the Invention

The present invention relates to an inspecting apparatus, more particularly to an apparatus for fastener inspection and sorting.

2. Description of the Related Art

Figure 1:
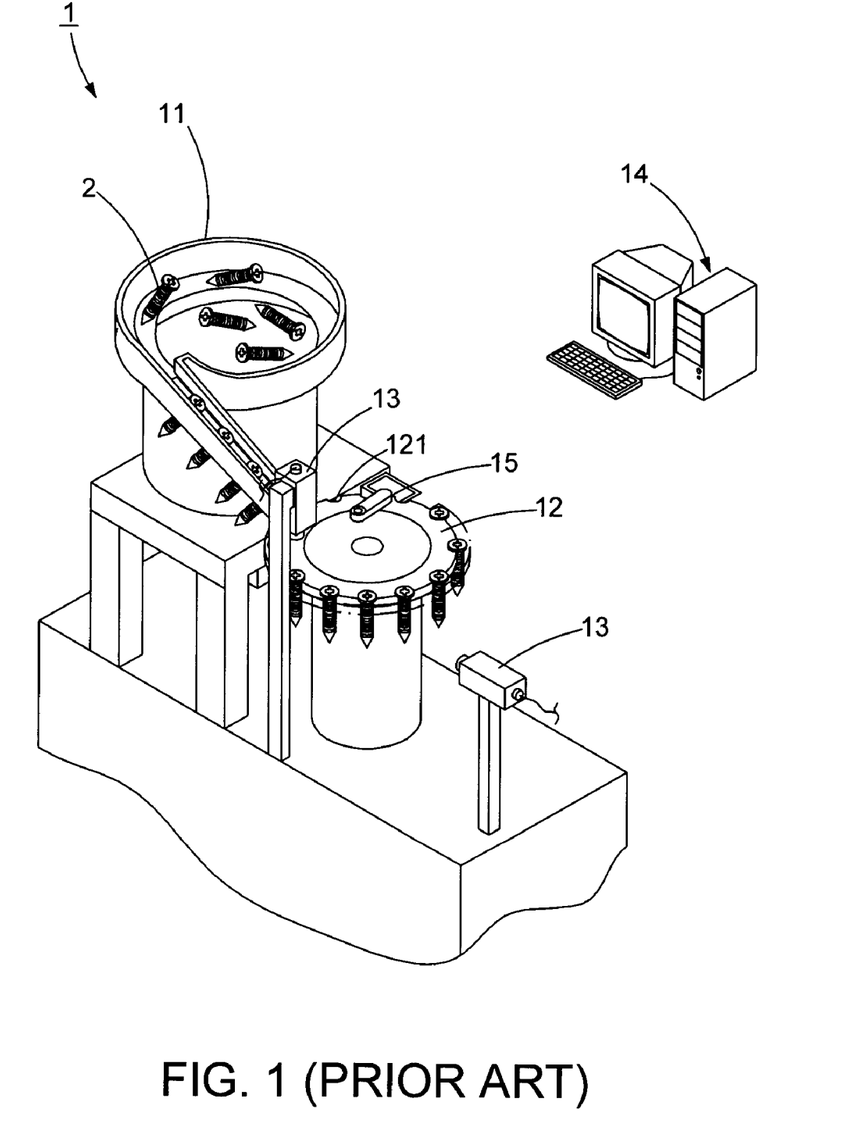
FIG. 1 is a perspective view showing a conventional invention.

Referring to FIG. 1, a conventional inspecting apparatus 1 is mainly comprised of an inlet feeding system 11 for aligning and positioning objects 2 (for instance of screws or nuts), a turntable 12 attached to the feeding system 11 with a plurality of cutout grooves 121 disposed thereon, two or more inspecting machines 13 disposed beside the turntable 12 for receiving signals of the screw 2, a determining device 14 electrically connected to the inspecting machines 13 for analyzing the signals, and a dispensing system 15 for sorting and discarding defective or malformed screws 2.

While in manipulation, the screw 2 is initially introduced into the groove 121 and positioned at the appropriate station by the turntable 12, so that the inspecting machines 13 respectively catches signals of the screw 2 in different directions and then transmits the signals to the determining device 14 for measuring and determining the quality thereof. Generally, each screw 2 has the defectives formed therearound while in a mass production, and the positions of these inspecting machines 13 usually restrict the views of the captured signals, namely each inspecting machine 13 merely performs in a single orientation and may ignore the defects occurred in other orientations, thus facilely resulting of the inaccurate determination in operation and affecting the detecting and sorting values.

SUMMARY OF THE INVENTION

The object of the present invention is to provide an apparatus for fastener inspection and sorting which is conducive to detect malformed defects occurred on the circumferential area of each object, simultaneously increase the inspecting quality and reduce the inaccurate determination.

The apparatus for fastener inspection and sorting in accordance with the present invention mainly provides with an inlet feeding system, a turntable with grooves formed thereon, an inspecting machine, a determining device and an outlet conveyer system. Particularly, an auxiliary device is disposed aside the turntable and comprised of a support base extended upon the grooves and a driving assembly attached to the base. Thus, the driving assembly assists the inspecting machine in capturing defect signals from different orientations of the target object either by driving the inspecting machine around the object or, by means of the magnetic attraction, gripping and spinning the target object within the detection range of the fixed inspecting machine. Therefore, the present invention facilitates to achieve accurate determinations, higher efficiency, and increase inspecting quality.

The advantages of the present invention over the known prior arts will become more apparent to those of ordinary skilled in the art by reading the following descriptions with the relating drawings.

DETAILED DESCRIPTION OF THE PREFERRED EMBODIMENTS

Before describing in greater detail, it should note that the like elements are denoted by similar reference numerals throughout the disclosure.

Figure 2:
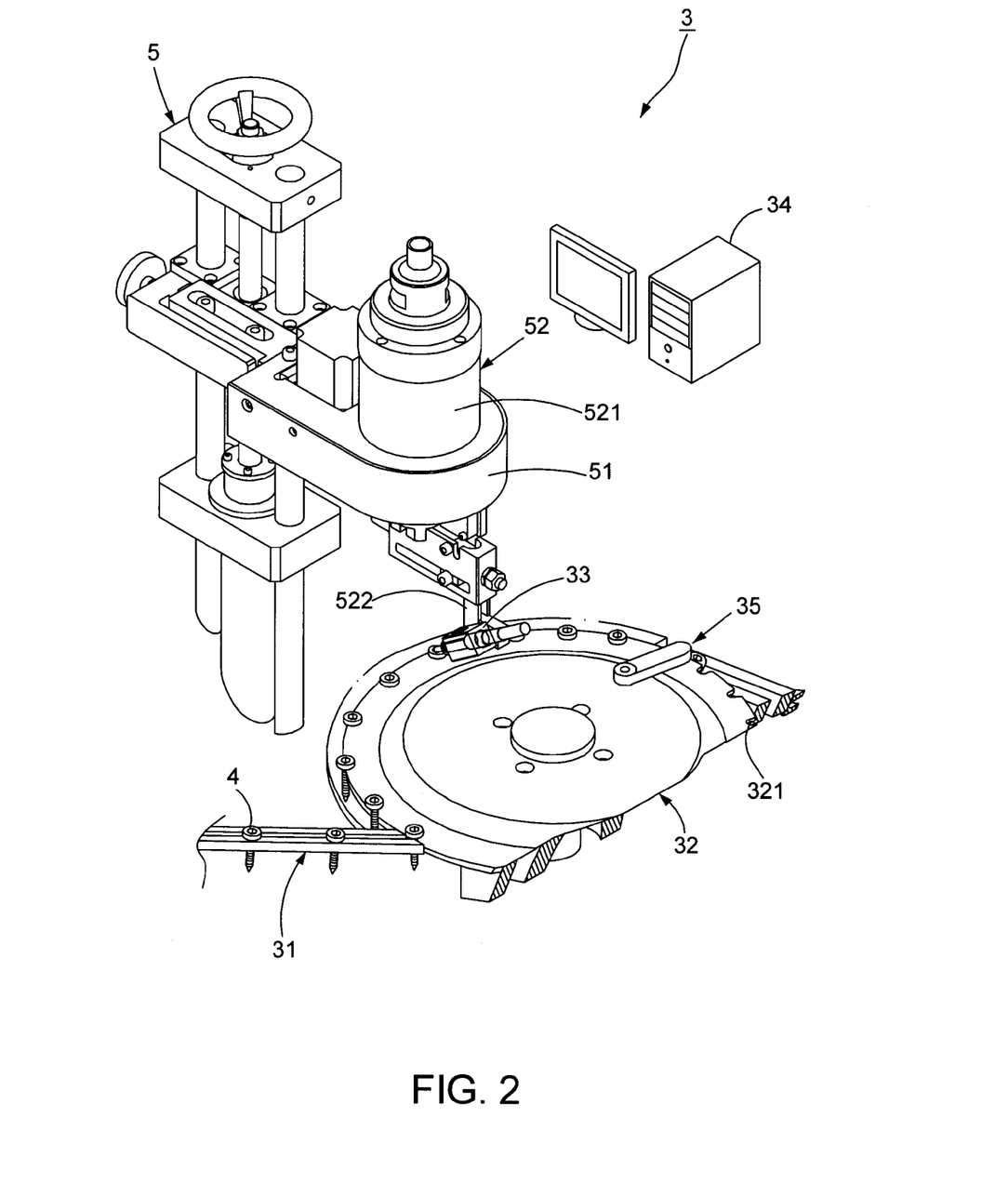
FIG. 2 is a perspective view showing a first preferred embodiment of the present invention.

Referring to FIG. 2, an apparatus 3 for fastener inspection and sorting of the first preferred embodiment comprises an inlet feeding system 31 for orientating and aligning objects 4, a turntable 32 connecting to an exit of the inlet feeding system 31 and having a plurality of grooves 321 formed in an outer periphery thereof, an inspecting machine 33 for performing signals of the objects 4, a determining device 34 electrically communicating with the inspecting machine 33 to analyze quality of the objects 4, and an outlet conveyer system 35 disposed at one side of the turntable 32 for sorting the objects 4 into defective and non-defective according to analyzed results of the determining device 34; wherein, the objects 4 can be screws or nuts and hereinafter screws are adopted. Additionally, the inspecting machine 33 is utilized by an eddy current inspecting probe in the following embodiments of the present invention.

Figure 3:
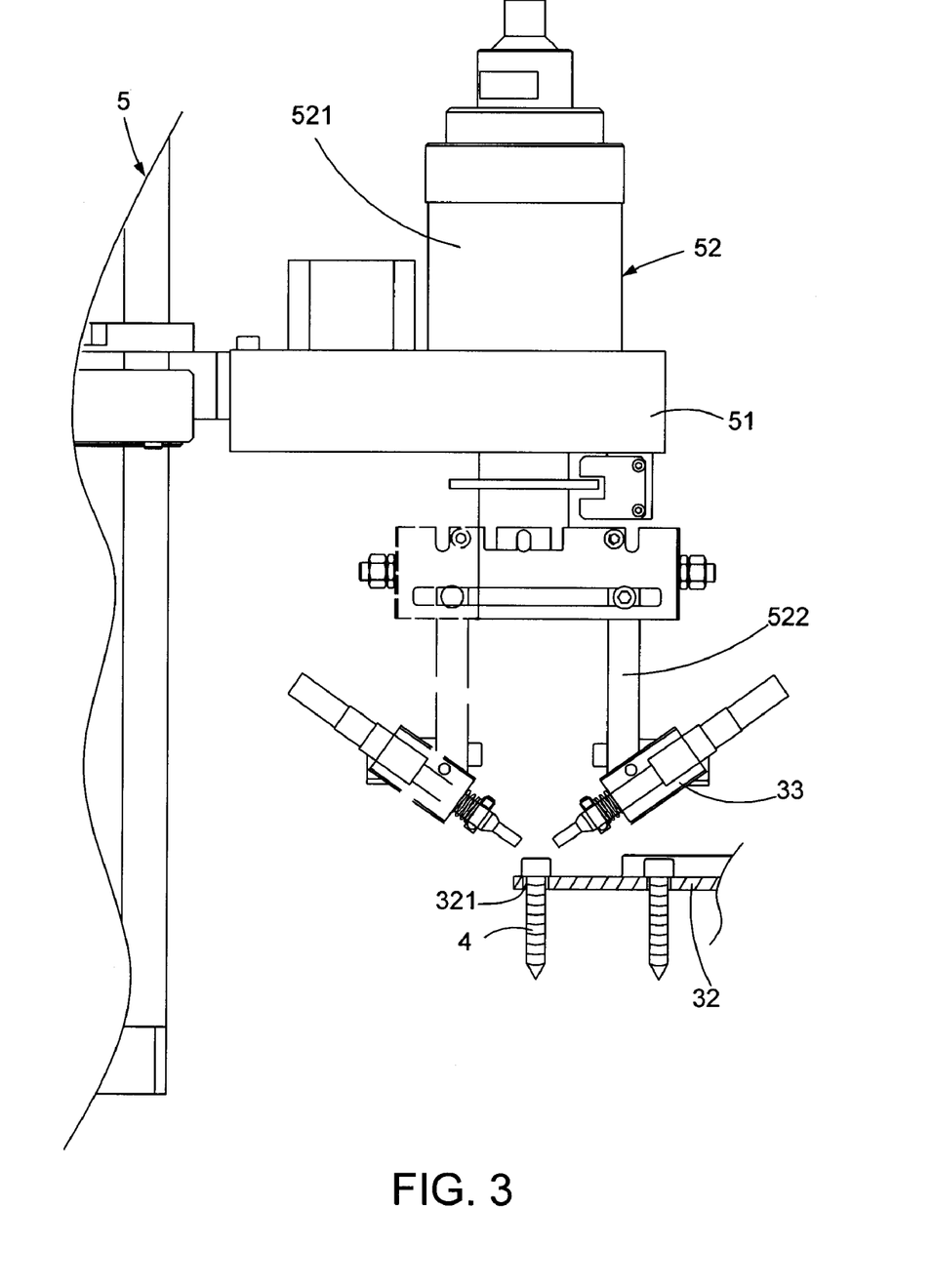
FIG. 3 is a schematic view showing the first embodiment in operation.

Further referring to FIG. 3, an auxiliary device 5 is disposed beside the turntable 32 and provides with a support base 51 located beside the turntable 32 and extended upon the grooves 321, and a driving assembly 52 which has a power source 521 pivoted to the support base 51 and a steering rod 522 having one end thereof connected to the inspecting machine 33 and its other end pivoted to the support base 51, thereby allowing the power source 521 to straight rotate the steering rod 522 as well as the inspecting machine 33.

Referring to FIG. 2 and 3, while operating, each object 4 is sequentially introduced into the groove 321 of the turntable 32 along the inlet feeding system 31 and further transferred to the appropriate detecting station, namely positioned under the support base 51 of the auxiliary device 5. Thereupon the power source 521 operatively drives the steering rod 522 rotating, and the inspecting machine 33 becomes revolving round the object 4 so as to capture circumferential defect signals thereof from different orientations. Subsequently, the captured signals are transmitted to the determining device 34 and analyzed thereby; further in view of the measuring result, the outlet conveyer system 35 would properly sort and discard the defective or malformed screw 4, thereby efficiently increasing the inspecting quality and reducing the inaccurate determination.

Figure 4:
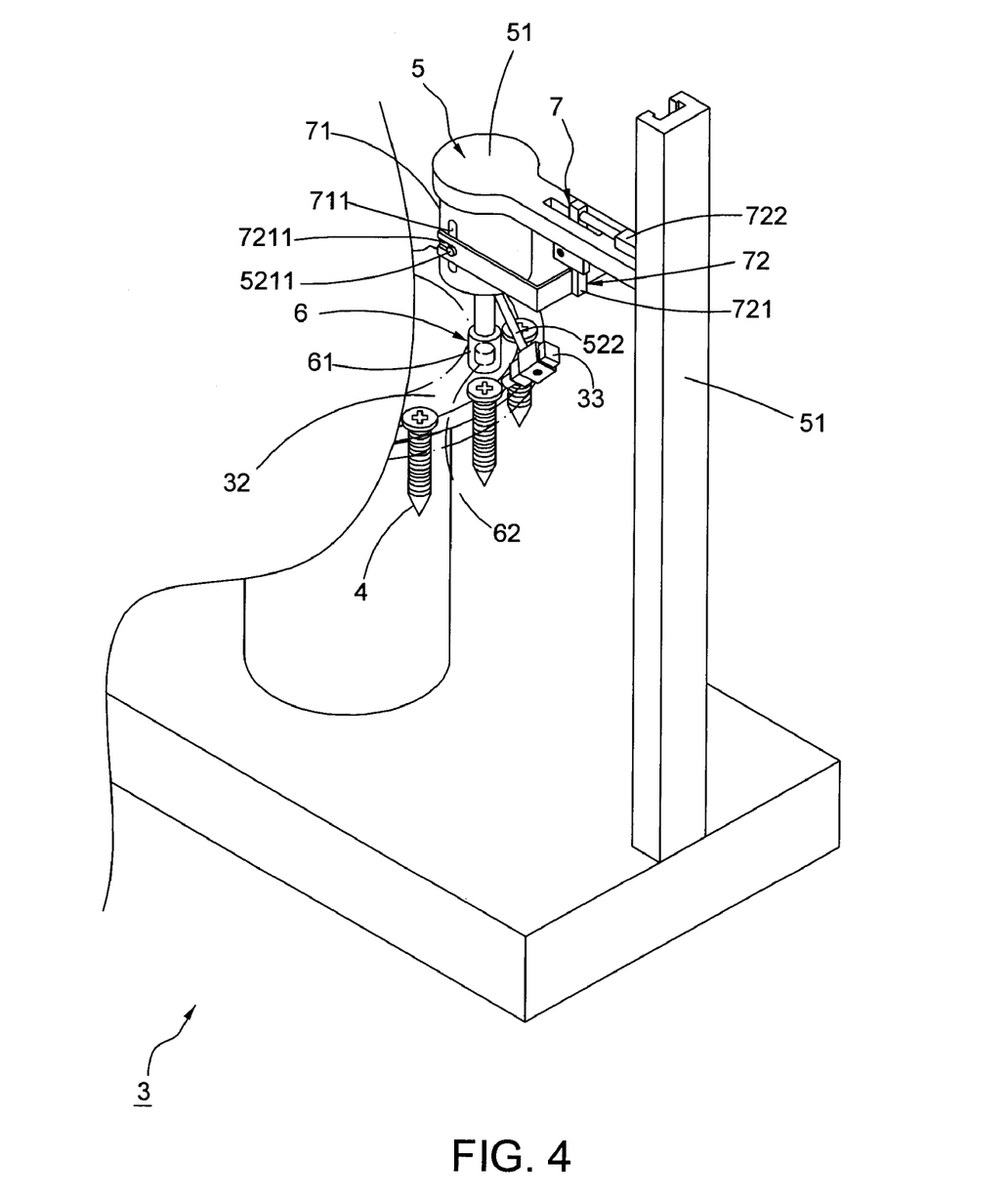
FIG. 4 is a perspective view showing a second preferred embodiment of the present invention.
Figure 5:
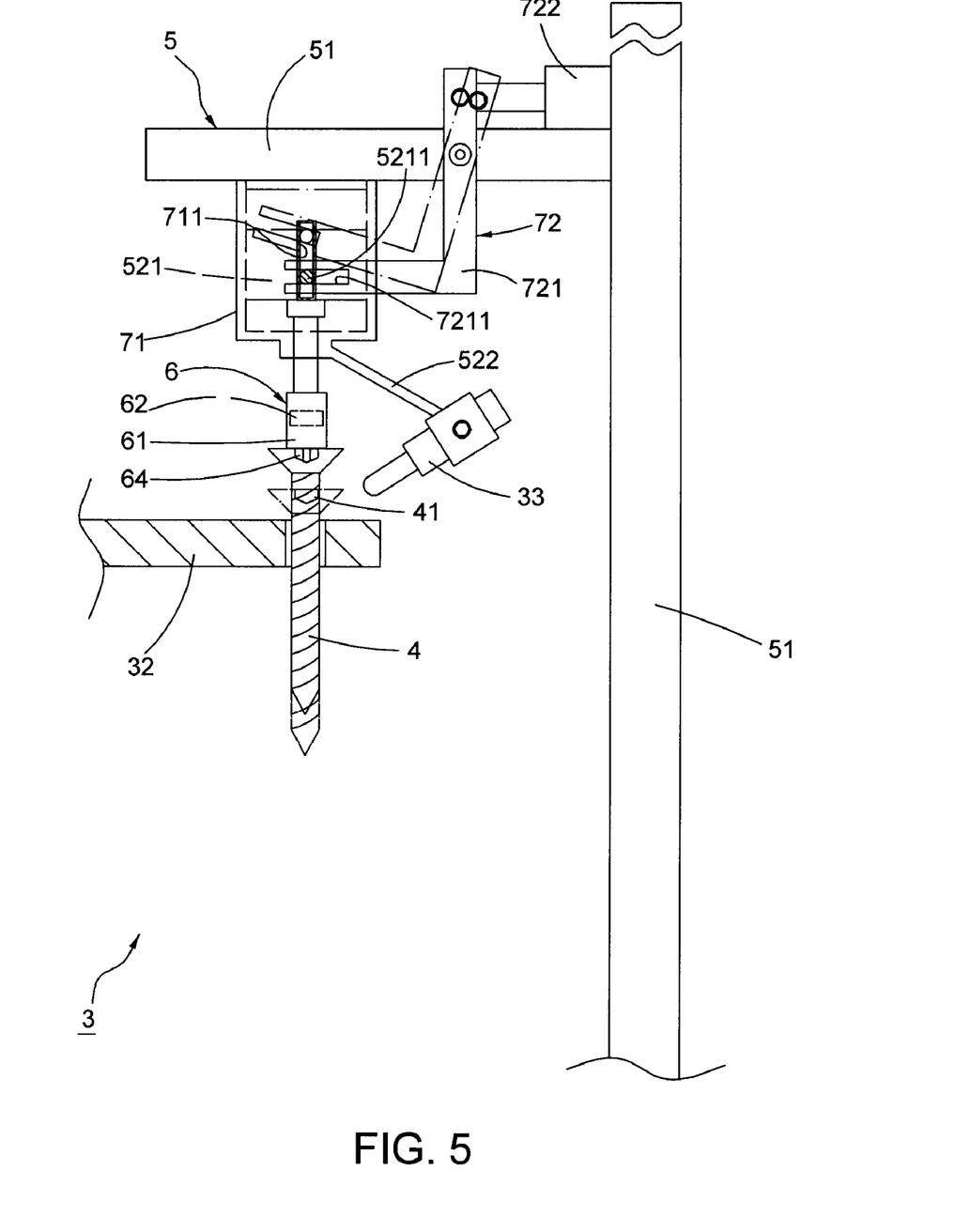
FIG. 5 is a schematic view showing the second embodiment in operation.

Referring to FIGS. 4 and 5, the second preferred embodiment of the present invention still has similar elements to the first embodiment; however their auxiliary devices 5 have respective formations by different installations. Particularly, a holding assembly 6 is pivoted to the auxiliary device 5 and provides with a holding base 61 attached to the power source 521 and driven thereby, and a propulsion device 7 for indirectly driving the power source 521; wherein, the holding base 61 includes a magnetic member 62 mounted therein and contains a drive plug 64 disposed at its free end for being formed complementary to a drive socket 41 of the object 4. The magnetic member 62 can be used by suitable materials, e.g. a permanent magnet or an electromagnet, and the permanent magnet is adopted to attract the object 4 in the present invention.

Figure 6:
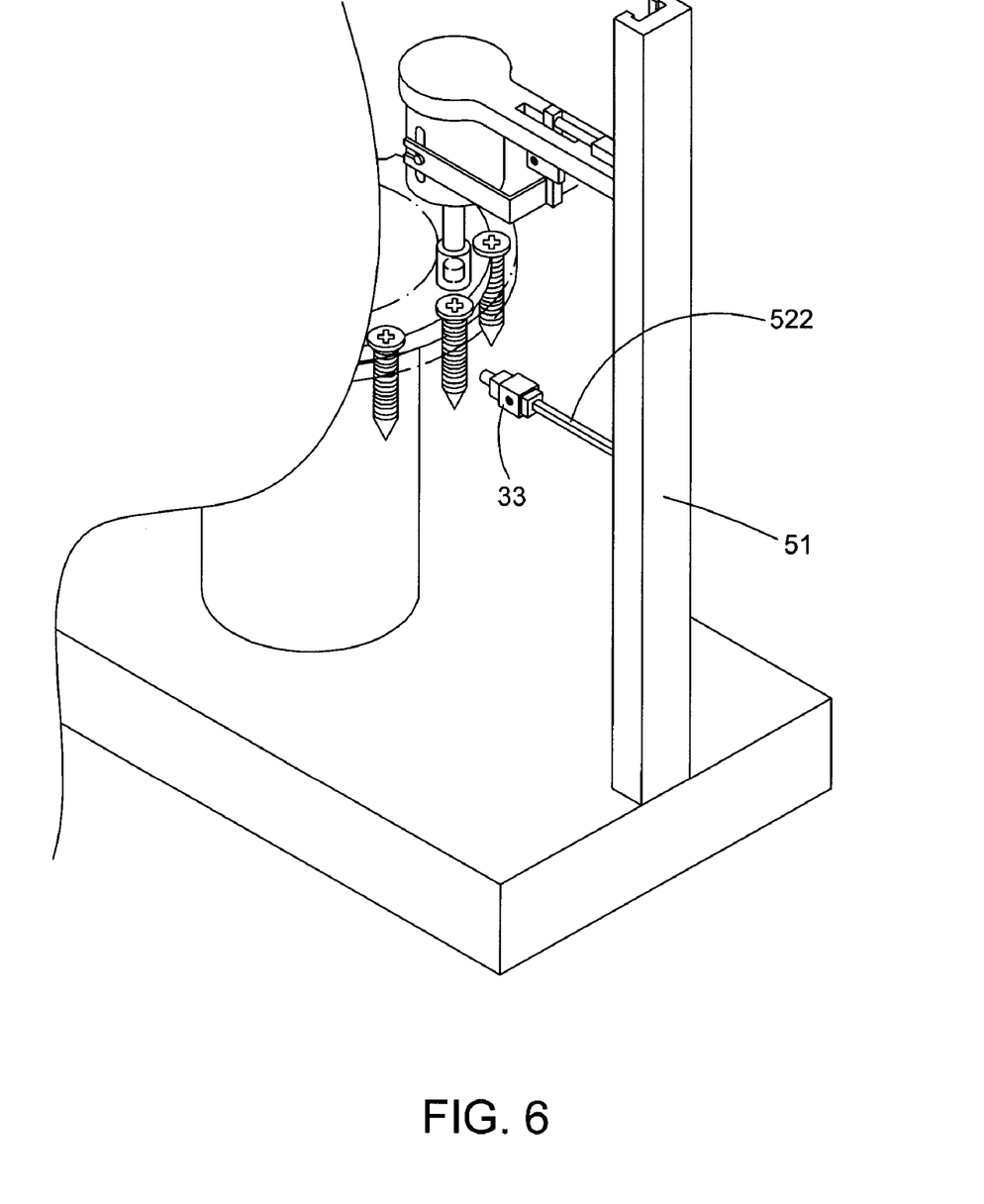
FIG. 6 is a perspective view showing a third preferred embodiment of the present invention.

Still further, the propulsion device 7 has a casing base 71 fastened to the support base 51 for disposing the power source 521 therein and a controlling device 72 pivotally mounted on the base 51. The casing base 71 further has a slot 711 arranged thereon and the power source 521 has a protrusion 5211 laterally disposed thereon for protruding out of the slot 711 and communicating with the controlling device 72. Additionally, the steering rod 522 can still has one end thereof connected to the inspecting machine 33 and other end to be fastened to the support base 51 (shown in FIG. 6), or the rod 522 changes its other end to be secured to the casing base 71 (shown in FIG. 4 and 5). The above two installations result in immobilizing the steering rod 522 and the inspecting machine 33. Moreover, the controlling device 72 includes a drive mean 721 disposed on the support base 51 and a motor drive unit 722 (e.g. a pneumatic cylinder) engaged to one end of the drive mean 721; wherein, the drive mean has a fork-like opening 7211 arranged on the other end thereof for clamping the protrusion 5211, thereby motivating the power source 521 to perform in upward and downward movements.

Referring to FIG. 5, in operation, the motor drive unit 722 begins to push the drive mean 721 forward while the object 4 is positioned under the holding base 61, whereby the protrusion 5211 is initially driven by the drive mean 721 to be moved downward along the slot 711 for descending the power source 521 and the holding base 61 as well. Further the magnetic member 62 substantially contacts the head of the object 4 and attracts it to be deviated from the turntable 32 when pulling the drive mean 721; subsequently, the power source 521 begins to drive the holding base 61 rotating and the object 4 also becomes spinning in the detection range of the immobilized inspecting machine 33, so that the inspecting machine 33 is able to perform defect detections of the object 4 from different orientations and passes the integral signals for the following inspections and dispensing, hence reducing the possibility of inaccurate determination and increasing the quality of the inspection and sorting. Finally, the turntable 32 merely pushes to relieve the object 4 of the attraction and restarts detecting the following object 4.

Figure 7:
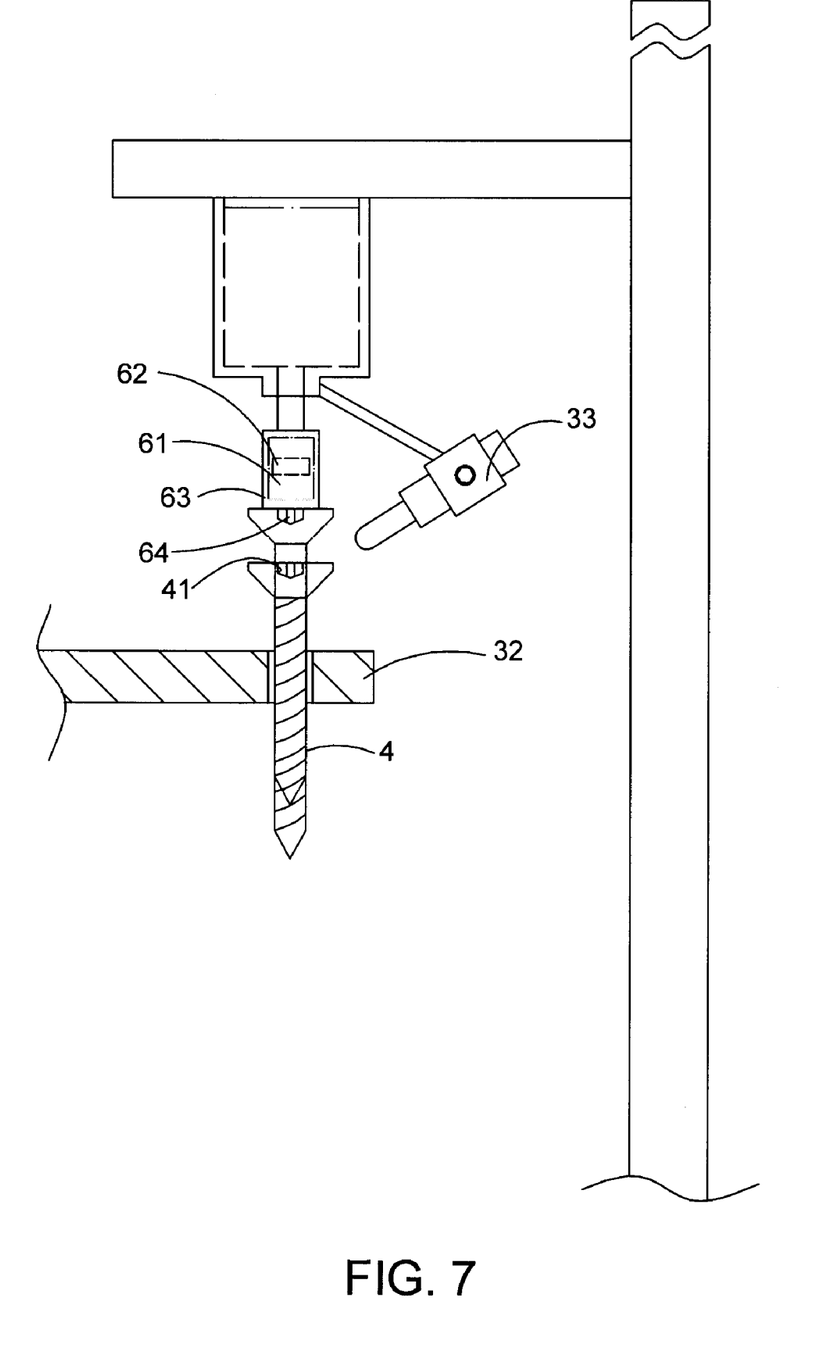
FIG. 7 is a schematic view showing a fourth preferred embodiment of the present invention.

Referring to FIG. 7, the fourth preferred embodiment of the present invention mainly comprises the concatenation of elements as the same as the second preferred embodiment. Differentially, the holding base 61 is wrapped by a shield 63. In this manner, the shield 63 assists to absorb the shock and the drive plug 64 inserted into the socket 41 prevents the object 4 from being swung when the magnetic member 62 attracts it out of the turntable 32. The subsequent procedures are the same as the previous embodiment and herein are omitted.

To sum up, the present invention takes advantages of the auxiliary device assisting in capturing the circumferential detection of each object from different orientations by directly driving the inspecting machine rotating or spinning the object under the magnetic attracting while immobilizing the inspecting machine, thereby obtaining accurate analyses with high efficiency and increasing the inspecting quality.

While we have shown and described the embodiment in accordance with the present invention, it should be clear to those skilled in the art that further embodiments may be made without departing from the scope of the present invention.

I claim:
1. An apparatus for fastener inspection and sorting comprising:
    an inlet feeding system for orientating and aligning objects;
    a turntable connecting to an exit of said inlet feeding system and including a plurality of grooves formed in an outer periphery thereof to receive and position said objects therein;
    an inspecting machine for performing signals of said objects;
    a determining device electrically communicating with said inspecting machine and analyzing said signals; and
    an outlet conveyer system disposed at one side of said turntable for sorting said objects into defective and non-defective according to analyzed results of said determining device;
    wherein an auxiliary device is disposed aside said turntable; said auxiliary device further comprising:
        a support base located beside said turntable and extended upon said grooves; and
        a driving assembly having a power source pivoted to said support base and a steering rod connected to said inspecting machine;
    wherein said steering rod has one end thereof attached to said inspecting machine and its other end pivoted to said support base, thereby permitting said power source to directly rotate said steering rod as well as said inspecting machine.

2. The apparatus as claimed in claim 1, further comprising a holding assembly pivoted to said auxiliary device, said holding assembly including a holding base attached to said power source and driven thereby; wherein said holding base includes a magnetic member mounted therein and a drive plug disposed at its free end.

3. The apparatus as claimed in claim 2, further comprising a propulsion device for indirectly driving said power source, said propulsion device including a casing base fastened to said support base for accommodating said power source and a controlling device pivoted thereto; said casing base having a slot arranged thereon whereby said power source protrudes therefrom; said controlling device including a drive means disposed on said support base and a motor drive unit engaged to one end of said drive means; said power source being attached to the other end of said drive means, thereby allowing removal of said power source from within said casing base.

4. The apparatus as claimed in claim 3, wherein said holding base is wrapped by a shield for shock absorbing.

5. An apparatus for fastener inspection and sorting comprising:
    an inlet feeding system for orientating and aligning objects;
    a turntable connecting to an exit of said inlet feeding system and including a plurality of grooves formed in an outer periphery thereof to receive and position said objects therein;
    an inspecting machine for performing signals of said objects;
    a determining device electrically communicating with said inspecting machine and analyzing said signals;
    an outlet conveyer system disposed at one side of said turntable for sorting said objects into defective and non-defective according to analyzed results of said determining device;
    wherein an auxiliary device is disposed aside said turntable; said auxiliary device further comprising:

a support base located beside said turntable and extended upon said grooves; and a driving assembly having a power source pivoted to said support base and a steering rod connected to said inspecting machine;

a holding assembly pivoted to said auxiliary device, said holding assembly including a holding base attached to said power source and driven thereby; wherein said holding base includes a magnetic member mounted therein and a drive plug disposed at its free end; and a propulsion device for indirectly driving said power source, which further has a casing base fastened to said support base for accommodating said power source and a controlling device pivoted thereto; wherein said casing base has a slot arranged thereon so that said power source protrudes therefrom; said controlling device includes a drive means disposed on said support base and a motor drive unit engaged to one end of said drive means; said power source further attached to the other end of said drive means, thereby facilitating removal of said power source from within said casing base.

6. The apparatus as claimed in claim 5, wherein said steering rod has one end thereof attached to said inspecting machine and its other end secured to said support base.

7. The apparatus as claimed in claim 5, wherein said steering rod has one end thereof attached to said inspecting machine and its other end secured to said casing base.

8. The apparatus as claimed in claim 5, wherein said holding base is wrapped by a shield for shock absorbing.

* * * * *